United States Patent [19]

Suzuki et al.

[11] Patent Number: 4,913,846
[45] Date of Patent: Apr. 3, 1990

[54] INFRARED ABSORBING COMPOSITION

[75] Inventors: Yoshiaki Suzuki; Gouichi Hayashi, both of Kanagawa, Japan

[73] Assignee: Fuji Photo Film Co., Ltd., Kanagawa, Japan

[21] Appl. No.: 82,004

[22] Filed: Aug. 5, 1987

[30] Foreign Application Priority Data

Aug. 5, 1986 [JP] Japan .................. 61-183947

[51] Int. Cl.⁴ .................. C07D 333/00; F21V 9/04
[52] U.S. Cl. .................. 252/587; 430/616
[58] Field of Search .................. 252/587; 546/2, 270, 546/6; 556/20, 113, 136, 137, 150, 270; 548/101, 108; 502/400, 401; 430/616

[56] References Cited

U.S. PATENT DOCUMENTS

| | | | |
|---|---|---|---|
| 3,588,216 | 6/1971 | Bloom | 252/587 |
| 3,620,888 | 11/1971 | Buzzell | 252/587 |
| 3,687,862 | 9/1972 | Bloom | 252/587 |
| 3,724,934 | 4/1973 | Bloom | 252/587 |
| 3,806,462 | 4/1979 | Bloom | 252/587 |
| 4,062,867 | 12/1977 | Bloom | 252/587 |
| 4,730,902 | 3/1988 | Suzuki et al. | 350/311 |
| 4,763,966 | 8/1988 | Suzuki et al. | 350/1.1 |
| 4,767,571 | 8/1988 | Suzuki et al. | 252/587 |

OTHER PUBLICATIONS

Dance, et al. "Solvatochromic Dithiolene . . . ", J.C.S. Chem. Comm. 1973, p. 433.
Rehorek, "Nickel (II)–Chelate", Z. Chem. 1976, 16(11), 451–2.
Kirmse, "Dithiolen", Z. Chem. 1977, 17(1), 33–5.
Rehorek, "Complexes with Copper", Z. Chem. 1977, 17(4), 149–50.

Primary Examiner—Alan L. Rotman
Assistant Examiner—Catherine S. Kilby Scalzo
Attorney, Agent, or Firm—Sughrue, Mion, Zinn, Macpeak & Seas

[57] ABSTRACT

An infrared absorbing composition is disclosed, which contains at least one compound selected from compounds represented by formula (I)

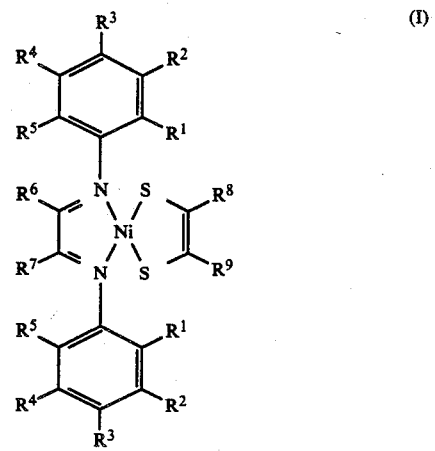

Compounds represented by formula (II)

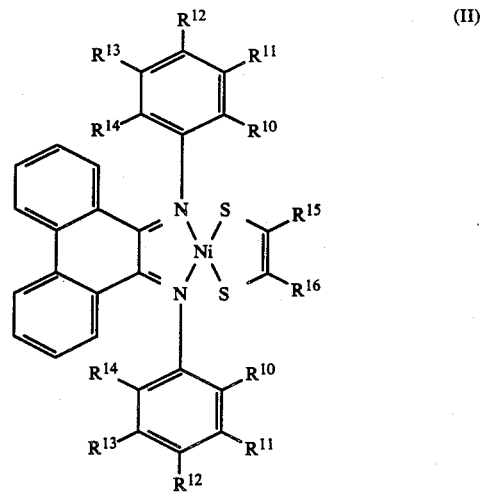

and compounds represented by formula (III)
(Abstract continued on next page.)

(III)

wherein $R^1$, $R^2$, $R^3$, $R^4$, $R^5$, $R^{10}$, $R^{11}$, $R^{12}$, $R^{13}$, $R^{14}$, $R^{17}$, $R^{18}$, $R^{19}$, $R^{20}$ and $R^{21}$, which may be the same or different, each represents a halogen atom, a hydrogen atom, or a substituted or unsubstituted alkyl, aryl, cycloalkyl or heterocyclic group which is bonded to the carbon atom of the benzene ring either directly or via a divalent linking group, or any pair of $R^1$ to $R^5$, $R^{10}$ to $R^{14}$, $R^{17}$ to $R^{21}$ having adjacent positions on the same ring combine to form a substituted or unsubstituted ring; $R^6$ and $R^7$, which may be the same or different, each represents an alkyl group or a substituted or unsubstituted aryl group; and $R^8$, $R^9$, $R^{15}$, $R^{16}$, $R^{22}$ and $R^{23}$, which may be the same or different, each represents a hydrogen atom, a substituted or unsubstituted alkyl group, a substituted or unsubstituted aryl group or a cyano group; or $R^8$ and $R^9$, $R^{15}$ and $R^{16}$, or $R^{22}$ and $R^{23}$ combine to form a substituted or unsubstituted ring, which may be condensed with one or more additional rings or ring systems which may be further substituted with substituents. The composition selectively absorbs far to near infrared rays having wavelengths of 600 nm or more and are useful as an optical filter.

13 Claims, 4 Drawing Sheets

INFRARED ABSORBING COMPOSITION

FIELD OF THE INVENTION

This invention relates to a near infrared absorbing composition, and more particularly to a near infrared absorbing composition which absorbs far to near infrared rays having wavelengths of 600 nm or more without substantially impairing transmission of visible rays.

BACKGROUND OF THE INVENTION

Compositions selectively absorbing far to near infrared rays having wavelengths of 600 nm or more have been demanded for their possible application to various fields, but none of the conventional infrared absorbing compositions has been satisfactory.

Near infrared absorbing substances are used in infrared cut filters, such as a safelight filter for near infrared-sensitive photographic materials, an infrared cut filter for human eyes, plastic films for plant growth control, a near infrared cut filter for semi-conductor photoreceptors, e.g., a silicone photodiode (SPD), and the like. Their properties to convert absorbed near infrared radiation to heat are utilized in heat-sensitive color formation or heat-sensitive recording by laser rays, photo disc recording layers, acceleration of ink drying, and the like. Further, they are coated on various light-sensitive materials as an antihalation layer to improve image qualities. In addition, attempts are being made to incorporate them in inks for laser beam-readable cards or inks for ink jet printers. Of these applications, five typical examples are described below in some detail.

(1) Safelight filters for infrared-sensitive light-sensitive materials:

In recent years, many silver halide light-sensitive materials have sensitivity to far to near infrared rays of 700 nm or more have been developed. Whether they are for black-and-white image formation or color image formation, or whether they are of ordinary type, instant type, or heat development type, they exhibit infrared-sensitivity to be used as false color films for exploitation of resources or to be exposed to light of a diode emitting infrared rays. In order to protect these light-sensitive materials from infrared light, safefilters for panchromatic films have been conventionally used.

(2) Plant growth control

Morphogenesis of plants relating to growth and differentiation, such as germination of seeds, growth of stems, development of leaves, formation of flower buds or tubers, etc., is known to be influenced by light and its study is known as photomorphogenesis.

Plastic films which selectively absorb light of 700 nm or more would be useful to control plant growth, for example, in such a manner that crops in a specific stage are covered with a near infrared absorbing film to retard earing-up (see Katsumi Inada, *Shokubutsu no Kagaku Chosetsu* (Chemical Control of Plants), Vol. 6, No. 1 (1971)).

(3) Heat radiation shielding

Radiation energy of sunlight in the near infrared and infrared regions having wavelengths of 800 nm or more is absorbed in objects and transformed into heat energy. Most part of the radiation energy distribution is concentrated to the near infrared region of from 800 to 2000 nm. Therefore, films which selectively absorb near infrared rays are extremely effective to shield the sun heat and useful to control a room temperature rise while sufficiently letting visible light in. Such films can be applied to horticultural greenhouse glazing, windows of houses, offices, shops or automobiles, aircraft glazing, and the like.

Conventionally employed heat radiation shields include plastic films on which a very thin metal layer is vacuum evaporated, and glass having dispersed therein inorganic compounds, e.g., FeO.

(4) Cut filters for human eyes to protect from harmful infrared rays

Infrared rays contained in the sunlight or light emitted during welding are harmful to human eye tissues. One of main uses of infrared cut filters is protection of human eyes from light containing such harmful infrared rays as in, for example, sunglasses and protective glasses for welders.

(5) Infrared cut filters for semi-conductor photoreceptors

Figure 4:
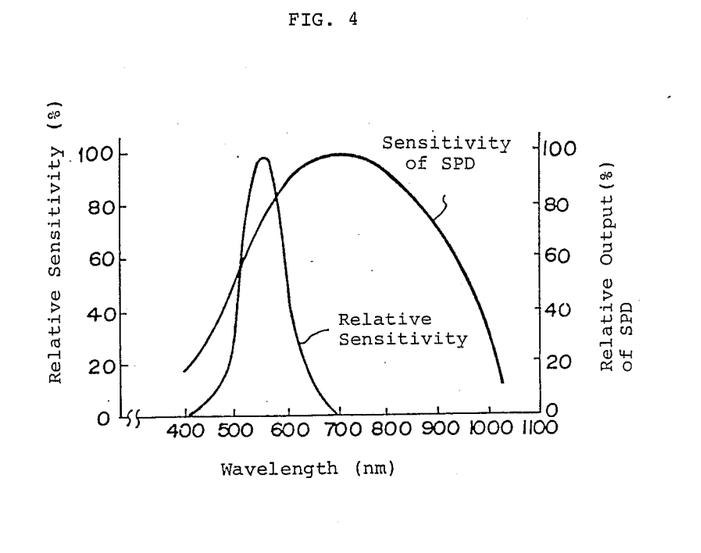
FIG. 4 is a graph showing the relative sensitivity of human eyes and of a silicone photodiode relative to light wavelength.

Light-detectors used in automatic exposure meters for cameras, etc. mainly employ a silicone photo-diode (SPD) as a photo-receptor. FIG. 4 shows a specific visibility curve and a graph of spectral sensitivity (i.e., relative outputs) of SPD. For use of SPD in exposure meters, it is necessary to cut the light in the infrared region that is not perceivable by human eyes to make the spectral sensitivity curve of the SPD approximate the specific visibility curve. In particular, the high outputs of SPD in the wavelength region of from 700 to 1100 nm to which human eyes are insensible cause working errors of exposure meters. Accordingly, plastic films which absorb light over the entire infrared region of from 700 to 1100 nm wavelength range would obviously increase the relative light transmittance in the visible region to increase the output of the SPD in that region, leading to marked improvements in the performance of exposure meters. In the conventional photo-detectors of this type, an infrared cut filter made of glass containing an inorganic infrared absorbent is fixed in front of the SPD.

Most of the organic dye type infrared absorbents which have been generally employed are not satisfactory in practical use due to their low light- and heat-resistance.

Further, filters used in the above-described various applications have the respective disadvantages as set forth below.

Conventional safelight filters for panchromatic films applied to use (1) above cannot sufficiently achieve their purpose as a safelight filter for infrared-sensitive photographic materials because they transmit not only green light of high visibility in part, but also a large quantity of infrared light, which causes light fog.

Plastic films having a metal deposit layer or glass having dispersed therein FeO applied to use (2) above strongly absorb light in not only the infrared region but also the visible region, resulting in reduced inner illumination, which causes an absolute decrease in sunshine, which is particularly detrimental in agricultural use.

The glass cut filters containing inorganic infrared absorbents applied to use (5) above are relatively resistant to heat and light, but have a low temperature in the visible region. This disadvantage has been coped with by increasing the sensitivity of the SPD. Increase of SPD sensitivity, however, leads to an increase of leakage current, which causes errors in working as a photo-detector, thus reducing reliability of the photo-detector. Further, the cut filters comprising inorganic substances lack the softness required in the production of photodetectors, and it is difficult, for the time being, to make improvements on the process of their production. Furthermore, inorganic infrared cut filters entail a cost for production which ultimately leads to the disadvantage of a greater cost for the resulting photo-detectors. Thus, although the photodetectors using the conventional inorganic cut filters show spectral sensitivity approximate to the specific visibility curve, they are disadvantageous from the standpoint of reduced working performance, increased cost for production, and difficulty in improving the production process.

In cases where complexes are used as an infrared absorbent for near infrared absorbing plastic films, difficulty in obtaining thin film formation is encountered due to their low solubility in organic solvents.

In the above-described applications of an infrared absorbing composition such as, for example, filters for an SPD, there is a demand for compositions to be formed in a very thin film and have high infrared absorption efficiency. To this effect, the composition should comprise a resin having dispersed therein a large quantity of an infrared absorbent. Therefore, the conventional infrared absorbents having low solubility in organic solvents do not meet this purpose.

In addition, since the near infrared absorbing plastic films containing metal complexes show a maximum absorption in a shorter wavelength, they are unsuitable for the increasing use of infrared absorbing plastic films in photoreceptors of semi-conductor lasers.

SUMMARY OF THE INVENTION

Accordingly, one object of this invention is to provide an infrared absorbent having an absorption maximum in the longer wavelength region, and particularly at 900 nm or more.

Another object of this invention is to provide a near infrared absorbent having high solubility in organic solvents and compatibility with film-forming binders.

As a result of extensive investigations, it has now been found that the above objects can be accomplished by an infrared absorbing composition containing at least one infrared absorbent selected from (α-diimine)(cis-1,2-ethylenedithiolate)nickel derivatives represented by formulae (I) to (III) shown below.

Formula (I) is represented by the formula

Formula (II) is represented by the formula

Formula (III) is represented by the formula wherein $R^1$, $R^2$, $R^3$, $R^4$, $R^5$, $R^{10}$, $R^{11}$, $R^{12}$, $R^{13}$, $R^{14}$, $R^{17}$, $R^{18}$, $R^{19}$, $R^{20}$ and $R^{21}$, which may be the same or different, each represents a halogen atom, a hydrogen atom, or a substituted or unsubstituted alkyl, aryl, cycloalkyl or heterocyclic group which is bonded to the carbon atom of the benzene ring either directly or via a divalent linking group, or any pair of $R^1$ to $R^5$, $R^{10}$ to $R^{14}$, and $R^{17}$ to $R^{21}$ having adjacent positions on the same ring of formulae (I), (II) and (III) may combine to form a substituted or unsubstituted ring; $R^6$ and $R^7$, which may be the same or different, each represents an alkyl group or a substituted or unsubstituted aryl group; $R^8$, $R^9$, $R^{15}$, $R^{16}$, $R^{22}$ and $R^{23}$, which may be the same or different, each represents a hydrogen atom, a substituted or unsubstituted alkyl group, a substituted or unsubstituted aryl group or a cyano group; or $R^8$ and $R^9$, $R^{15}$ and $R^{16}$, or $R^{22}$ and $R^{23}$ may combine to form a substituted or unsubstituted ring, which may be condensed with another ring or ring system which is further substituted with substituents.

DETAILED DESCRIPTION OF THE INVENTION

In formulae (I), (II) and (III), the halogen atom represented by $R^1$, $R^2$, $R^3$, $R^4$, $R^5$, $R^{10}$, $R^{11}$, $R^{12}$, $R^{13}$, $R^{14}$, $R^{17}$, $R^{18}$, $R^{19}$, $R^{20}$ and $R^{21}$ includes a fluorine atom, a chlorine atom, a bromine atom, and an iodine atom.

The alkyl group represented by $R^1$ to $R^5$, $R^{10}$ to $R^{14}$, or $R^{17}$ to $R^{21}$ preferably contains from 1 to 20 carbon atoms and may be either a straight chain alkyl group or a branched chain alkyl group. Examples of the straight or branched chain alkyl group are a methyl group, an ethyl group, a propyl group, a butyl group, a hexyl group, an octyl group, a decyl group, a dodecyl group, a tetradecyl group, a hexadecyl group, and an octadecyl group.

The aryl group represented by $R^1$ to $R^5$, $R^{10}$ to $R^{14}$, or $R^{17}$ to $R^{21}$ preferably contains from 6 to 14 carbon atoms and includes, for example, a phenyl group and a naphthyl group.

The heterocyclic group or cycloalkyl group represented by $R^1$ to $R^5$, $R^{10}$ to $R^{14}$, or $R^{17}$ to $R^{21}$ is preferably a 5- to 6-membered ring. The heterocyclic group contains at least one nitrogen atom, oxygen atom, or sulfur atom as a hetero atom. Examples of the heterocyclic group are a furyl group, a hydrofuryl group, a thienyl group, a pyrrole group, a pyrrolidyl group, a pyridyl group, an imidazolyl group, a pyrazolyl group, a quinolyl group, an indolyl group, an oxazolyl group, and a thiazolyl group. Examples of the cycloalkyl group are a cyclopentyl group, a cyclohexyl group, a cyclohexenyl group, and a cyclohexadienyl group.

The ring jointly formed by adjacent $R^1$ to $R^5$, $R^{10}$ to $R^{14}$, and $R^{17}$ to $R^{21}$ groups is preferably a 6-membered ring and specifically includes a benzene ring, a naphthalene ring, an isobenzothiophene ring, an isobenzofuran ring, and an isoindoline ring. Of these, a substituted or unsubstituted benzene ring or a substituted or unsubstituted benzene ring condensed with one or more additional rings or ring systems which may be substituted or unsubstituted is more preferred.

The aforesaid alkyl, cycloalkyl, aryl or heterocyclic group may be bonded to the carbon atom of the benzene ring via a divalent linking group, such as an oxy group (—O—), a thio group (—S—), an amino group, an oxycarbonyl group, a carbonyl group, a carbamoyl group, a sulfamoyl group, a carbonylamino group, a sulfonyl group, and a carbonyloxy group.

Examples of the alkyl group bonded to the benzene ring via the divalent linking group include an alkoxy group (e.g., a methoxy group, an ethoxy group, a butoxy group, a propoxy group, an n-decyloxy group, an n-dodecyloxy group, an n-hexadecyloxy group, etc.), an alkoxycarbonyl group (e.g., a methoxycarbonyl group, an ethoxycarbonyl group, a butoxycarbonyl group, an n-decyloxycarbonyl group, an n-hexadecyloxycarbonyl group, etc.), an acyl group (e.g., an acetyl group, a valeryl group, a stearoyl group, etc.), an acyloxy group (e.g., an acetoxy group, a hexadecylcarbonyloxy group, etc.), an alkylamino group (e.g., an n-butylamino group, an N,N-diethylamino group, an N,N-didecylamino group, etc.), an alkylsulfamoyl group (e.g., a butylsulfamoyl group, an N,N-diethylsulfamoyl group, an n-dodecylsulfamoyl group, etc.), a sulfonylamino group (e.g., a methylsulfonylamino group, a butylsulfonylamino group, etc.), a sulfonyl group (e.g., a mesyl group, an ethanesulfonyl group, etc.), an acylamino group (e.g., an acetylamino group, a valerylamino group, a palmitoylamino group, a benzoylamino group, a toluoylamino group, etc.), and the like.

Examples of the cycloalkyl group bonded to the benzene ring via the aforesaid divalent linking group include a cyclohexyloxy group, a cyclohexylcarbonyl group, a cyclohexyloxycarbonyl group, a cyclohexylamino group, a cyclohexenylcarbonyl group, a cyclohexenyloxy group, etc.

Examples of the aryl group bonded to the benzene ring via the aforesaid divalent linking group include an aryloxy group (e.g., a phenoxy group, a naphthoxy group, etc.), an aryloxycarbonyl group (e.g., a phenoxycarbonyl group, a naphthoxycarbonyl group, etc.), an acyl group (e.g., a benzoyl group, a naphthoyl group, etc.), an anilino group (e.g., a phenylamino group, an N-methylanilino group, an N-acetylanilino group, etc.), an acyloxy group (e.g., a benzoyloxy group, a toluoyloxy group, etc.), an arylcarbamoyl group (e.g., a phenylcarbamoyl group, etc.), an arylsulfamoyl group (e.g., a phenylsulfamoyl group, etc.), an arylsulfonylamino group (e.g., a phenylsulfonylamino group, a p-tolylsulfonylamino group, etc.), an arylsulfonyl group (e.g., a benzenesulfonyl group, a tosyl group etc.), an acylamino group (e.g., a benzoylamino group, etc.), and the like.

The alkyl, aryl, heterocyclic or cycloalkyl group represented by $R^1$ to $R^5$, $R^{10}$ to $R^{14}$, or $R^{17}$ to $R^{21}$ or the 6-membered ring jointly formed by these groups adjacent to each other, which may or may not be condensed with one or more additional rings or ring systems may have substituents, such as a halogen atom (e.g., a chlorine atom, a bromine atom, a fluorine atom, etc.), a cyano group, a hydroxyl group, a straight or branched chain alkyl group (e.g., a methyl group, an ethyl group, a propyl group, a butyl group, a hexyl group, an octyl group, a decyl group, a dodecyl group, a tetradecyl group, a hexadecyl group, a heptadecyl group, an octadecyl group, a methoxyethoxyethyl group, etc.), an aryl group (e.g., a phenyl group, a tolyl group, a naphthyl group, a chlorophenyl group, a methoxyphenyl group, an acetylphenyl group, etc.), an alkoxy group (e.g., a methoxy group, an ethoxy group, a butoxy group, a propoxy group, a methoxyethoxy group, etc.), an aryloxy group (e.g., a phenoxy group, a tolyloxy group, a naphthoxy group, a methoxyphenoxy group, etc.), an alkoxycarbonyl group (e.g., a methoxycarbonyl group, a butoxycarbonyl group, a phenoxymethoxycarbonyl group, etc.), an aryloxycarbonyl group (e.g., a phenoxycarbonyl group, a tolyloxycarbonyl group, a methoxyphenoxycarbonyl group, etc.), an acyl group (e.g., a formyl group, an acetyl group, a valeryl group, a stearoyl group, a benzoyl group, a toluoyl group, a naphthoyl group, a p-methoxybenzoyl group, etc.), an acyloxy group (e.g., an acetoxy group, a benzoyloxy group, etc.), an acylamino group (e.g., an acetoxyamido group, a benzamido group, a methoxyacetamido group, etc.), an anilino group (e.g., a phenylamino group, an N-methylanilino group, an N-phenylanilino group, an N-acetylanilino group, etc.), an alkylamino group (e.g., an n-butylamino group, an N,N-diethylamino group, a 4-methoxy-n-butylamino group, etc.), a carbamoyl group (e.g., an n-butylcarbamoyl group, an N,N-diethylcarbamoyl group, etc.), a sulfamoyl group (e.g., an n-butylsulfamoyl group, an N,Ndiethylsulfamoyl group, an n-dodecylsulfamoyl group, an N-(4-methoxy-n-butyl)sulfamoyl group, etc.), a sulfonylamino group (e.g., a methylsulfonylamino group, a phenylsulfonylamino group, a methoxymethylsulfonylamino group, etc.), a sulfonyl group (e.g., a mesyl group, a tosyl group, a methoxymethanesulfonyl group, etc.), and so on.

The alkyl group represented by $R^6$ or $R^7$ preferably contains from 1 to 20 carbon atoms and includes, for example, a methyl group, an ethyl group, an n-butyl group, an n-hexyl group, an n-octyl group, an n-dodecyl group, an n-hexadecyl group, etc. The aryl group represented by $R^6$ or $R^7$ preferably includes a phenyl group or a phenyl group substituted with, for example, a methyl group, a methoxy group or a halogen atom.

The alkyl group represented by $R^8$, $R^9$, $R^{15}$, $R^{16}$, $R^{22}$ or $R^{23}$ preferably contains from 1 to 20 carbon atoms and includes, for example, a methyl group, an ethyl group, an n-butyl group, an n-hexyl group, an n-octyl group, an n-dodecyl group, an n-hexadecyl group, etc. The alkyl group may have substituents, such as an alkyl group having from 1 to 20 carbon atoms (e.g., a methyl group, an ethyl group, an n-butyl group, an n-octyl group, etc.) and an alkoxy group having from 1 to 20 carbon atoms (e.g., a methoxy group, an ethoxy group, an n-butoxy group, etc.).

The aryl group represented by $R^8$, $R^9$, $R^{15}$, $R^{16}$, $R^{22}$ or $R^{23}$ preferably includes a phenyl group or a phenyl group substituted with, for example, an alkyl group having from 1 to 20 carbon atoms (e.g., a methyl group, an ethyl group, an n-butyl group, an n-octyl group, an n-decyl group, etc.), an alkoxy group having from 1 to 20 carbon atoms (e.g., a methoxy group, an ethoxy group, an n-butoxy group, an n-dodecyloxy group, etc.), etc.

The ring jointly formed by $R^8$ and $R^9$, $R^{15}$ and $R^{16}$, or $R^{22}$ and $R^{23}$ preferably includes a substituted or unsubstituted 5- or 6-membered ring including a ring condensed with one or more additional rings or ring systems which may be further substituted with substituents, and may contain a hetero atom (e.g., an oxygen atom, a nitrogen atom, a sulfur atom, etc.). The substituents therefor include a halogen atom, an alkyl group, an alkoxy group, and a cyano group.

Specific but non-limiting examples of the compounds represented by formulae (I), (II) and (III) that are preferably used in the present invention are shown below.

(1)

(2)

(3)

(4)

(5)

(6)

(7)

(8)

(9)

(10)

(11)

(12)

(13)

(14)

(15)

(16)

(17)

(18)

(19)

(20)

(21)

-continued (22)

(23)

(24)

-continued (25)

(26)

Absorption maxima ($\lambda_{max}$), molecular extinction coefficients ($\epsilon_{max}$ unit: $l.mol^{-1}.cm^{-1}$), and melting points (decomposition points) of some of these compounds are shown in Table 1 below. In the Table, $\lambda_{max}$ and $\epsilon_{max}$ are values as determined in $CH_2Cl_2$ unless otherwise indicated.

TABLE 1

| Compound No. | $\lambda_{max}$ (nm) | $\epsilon_{max}$ ($\times 10^4$) | Melting Point (°C.) |
|---|---|---|---|
| (2) | 781 | 0.88 | 212 |
| (11) | 780 | 0.79 | 215–220 |
| (19) | 756 | 1.15 | 164–166 |
| (20) | 754 | 0.94 | 265–270 |
| (21) | 754 | 0.91 | 179–195 |
| (22) | 766 | 1.07 | 195–197 |
| (23) | 754 | 1.00 | 166–169 |
| (24) | 756 | 0.98 | 171–174 |
| (25) | 756 | 0.90 | 164–167 |
| (26) | 756 | 0.96 | 148–153 |
| (27) | 754 | 0.97 | 163–170 |
| (28) | 762 | 0.77 | 118–120 |
| (33) | 775 | 0.97 | 233–238 |
| (34) | 780 | 1.06 | 240–243 |
| (35) | 770 | 1.11 | 200–202 |
| (38) | 774 | 0.88 | 210–212 |
| (47) | 690 | 0.92 | 259–262 |
| (48) | 688 | 0.90 | 245–247 |
| (51) | 735 | 0.79 | >300 |
| (52) | 728 | 0.77 | 220–223 |
| (53) | 727 | 0.62 | 185–188 |
| (54) | 729 | 0.63 | 174–189 |
| (55) | 725 | 0.73 | 214–217 |
| (56) | 723 | 0.59 | 170–176 |
| (57) | 760 | 0.88 | >300 |
| (60) | 580 | 0.44 | 254–260 |
| (70) | 830 | 1.94 | 233–236 |
| (71) | 828 | 1.64 | 251–255 |

TABLE 1-continued

| Compound No. | $\lambda_{max}$ (nm) | $\epsilon_{max}$ (× 10⁴) | Melting Point (°C.) |
|---|---|---|---|
| (76) | 830 | 2.00 | 259–263 |
| (103) | 930 | 2.75 | 208–212 |
| (108) | 860 | 1.60 (DMF) | 223–226 |
| (113) | 770 | 1.56 | 258–270 |
| (114) | 766 | 1.60 | >300 |
| (115) | 768 | 1.67 | 233–237 |
| (116) | 765 | 1.47 | 188–191 |
| (117) | 764 | 1.54 | 273–277 |
| (118) | 782 | 1.44 | >300 |
| (137) | 680 | 1.25 | >300 |
| (147) | 844 | 0.92 | 245–250 |

The (α-diimine)(cis-1,2-ethylenedithiolate)nickel derivatives represented by formulae (I), (II) and (III) can generally be synthesized as follows.

A cis-1,2-ethylenedithiol derivative or an alkali metal salt thereof is dissolved in absolute methanol. To the solution (which may be prepared from a precursor of the cis-1,2-ethylenedithiol derivative) is added a bis(α-diimine)nickel (II) halide or an (α-diimine)(dihalo)-nickel (II) complex in the form of a powder or a solution in methanol, followed by stirring. The formed precipitate is collected by filtration and extracted with an organic solvent, e.g., dichloromethane. The extract is concentrated, and methanol is slowly added to the concentrate to obtain crystals of the desired complex.

Typical examples for synthesis of the compounds of formulae (I) to (III) are described below. Various bis(α-diimine)nickel halides or (α-diimine)(dihalo)nickel complexes used as a starting material in the synthesis were prepared in accordance with the processes disclosed in Z. Anorg. Allg. Chemie, Vol. 267, 137 and 161 (1951). In the following synthesis examples, these starting materials are inclusively abbreviated as (α-diimine)(dihalo)-nickel and unless otherwise indicated, all parts, percents, ratios and the like are by weight.

SYNTHESIS EXAMPLE 1

Synthesis of Compound (2)

In 30 ml of absolute methanol was dispersed 0.002 mol of 4,5-dimethyl-1,3-dithiol-2-one, and 0.004 mol of sodium methoxide or a methanolic solution thereof was added thereto, followed by stirring at room temperature for 2 hours. To the resulting solution was added 0.002 mol of (α-diimine)(dichloro)nickel, and the mixture was stirred at room temperature for 1 hour. The precipitate thus formed was filtered, washed with methanol, and air-dried. The resulting solid was dissolved in a small amount of dichloromethane and subjected to column chromatography using silica gel (Merck Art 7734 Kieselgel 60; 70–230 mesh) to obtain 0.2 g of Compound (2).

SYNTHESIS EXAMPLE 2

Synthesis of Compound (21)

In 30 ml of absolute methanol was dispersed 0.002 mol of 4,5-diphenyl-1,3-dithiol-2-one, and 0.004 mol of sodium methoxide or a methanolic solution thereof was added thereto, followed by stirring at room temperature for 2 hours. To the resulting solution was added 0.002 mol of (α-diimine)(dichloro)nickel, and the mixture was stirred at room temperature for 1 hour. The formed precipitate was filtered, washed with methanol, and air-dried. The resulting solid was dissolved in a small amount of dichloromethane and purified by column chromatography using silica gel (Merck Art 7734 Kieselgel 60; 70–230 mesh) to obtain 0.3 g of Compound (21).

SYNTHESIS EXAMPLE 3

Synthesis of Compound (115)

In 30 ml of absolute methanol was dissolved 0.002 mol of (α-diimine)(dibromo)nickel, and 0.002 mol of sodium 1,2-dicyanoethylenedithiolate was added to the solution, followed by stirring at room temperature for 2 hours. The precipitated crystals were filtered, washed with methanol, and air-dried. The resulting solid was dissolved in a small amount of dichloromethane and purified by column chromatography using silica gel (Merck Art 7734 Kieselgel 60; 70–230 mesh) to obtain 0.1 g of Compound (115).

The infrared absorbing composition according to the present invention comprises at least one of the compounds represented by formulae (I), (II) and (III) and an appropriate binder. The binders to be used are not particularly limited, and any of organic or inorganic substances that may not impair the infrared absorbing properties of the compounds of the invention can be employed. Usable binders include high polymeric substances, such as plastics, and inorganic materials, such as glass. Of these binders, preferred are those capable of forming films excellent in transparency and mechanical properties. Such film-forming binders include polyesters typically exemplified by polyethylene terephthalate, cellulose esters, e.g., cellulose diacetate, cellulose triacetate, cellulose acetate butyrate, etc., polyolefins, e.g., polyethylene, polypropylene, etc., polyvinyl compounds, e.g., polyvinyl chloride, polyvinylidene chloride, vinyl chloride-vinyl acetate copolymers, polystyrene, etc., acrylic addition polymers, e.g., polymethyl methacrylate, etc., polycarbonates comprising polycarbonic acid esters, phenolic resins, urethane resins, and hydrophilic binders, e.g., gelatin, and the like.

For film formation, a first method comprises incorporating the compound of formula (I), (II) or (III) into plastics. For example, the compound is mixed with various additives to obtain a compound in the form of a powder or pellet, which is then melt-extruded by T-die extrusion or blown-film extrusion or calendered to form a film having uniformly dispersed therein the compound of formula (I), (II) or (III). In the case of film casting, the compound is added to a polymer solution to be cast.

A second film formation method comprises coating a polymer solution or dispersion containing the compound on a plastic or glass substrate to form an infrared absorbing layer. The binder to be used in this method is selected from polymers which are capable of dissolving the compound of the present invention as much as possible and also exhibit excellent adhesion to the plastic or glass substrate. Polymeric binders meeting these requirements include polymethyl methacrylate, cellulose acetate butyrate, polycarbonate, and the like. In order to ensure adhesion to the substrate, a subbing layer may be provided on the substrate.

A third film formation method comprises mixing the compound of the present invention and a polymerizable monomer(s) in a light incident window frame of an element where infrared rays should be cut, adding an appropriate polymerization initiator to the mixture, and applying heat or light thereto to induce polymerization to thereby form a polymer filter in situ. According to this method, it is possible to envelop the whole element with plastics formed from an ethylenically unsaturated polymerizable monomer or an addition polymerizable composition, e.g., an epoxy resin.

A fourth method comprises vacuum evaporation of the compound of the present invention onto an appropriate substrate. In this case, an appropriate film-forming binder may further be coated on the deposit to form a protective layer.

The near infrared absorbent according to the present invention can be utilized in solid-state color image sensing device according to an embodiment (1) wherein a color separation filter layer having a plurality of prescribed spectral characteristics in a stripe or mosaic form is formed, and a surface protective layer containing the near infrared absorbent is formed on the filter layer or the infrared absorbent is vacuum deposited on the filter layer; an embodiment (2) where the near infrared absorbent of the invention is incorporated in the color separation filter layer together with visible light absorbing dyes, etc., or an embodiment (3) where the near infrared absorbent is incorporated into a transparent intermediate layer or a smooth surface layer of a multilayer color separation filter. Optical filters obtained by the infrared absorbing composition of the present invention are particularly effective when used in combination with color separation filters described in Japanese patent application (OPI) Nos. 58107/82, 9317/84 and 30509/84 (the term "OPI" as used herein means "unexamined published application").

The infrared absorbing composition according to the present invention can contain two or more compounds of formulae (I), (II) and (III). If desired, the composition can further contain known organic or metal complex type near infrared absorbents in combination. In particular, a combined use with an absorbent having an absorption maximum different from that of the compound of the invention broadens the absorbable wavelength region.

In order to improve light resistance of the infrared absorbing composition, adding ultraviolet absorbents is effective. Examples of ultraviolet absorbents which can be used in combination include substituted or unsubstituted benzoic acid esters, e.g., resorcin monobenzoate, methyl salicylate, etc.; cinnamic acid esters, e.g., butyl 2-oxy-3-methoxycinnamate, etc.; benzophenones, e.g., 2,4-dioxybenzophenone, etc.; $\alpha,\beta$-unsaturated ketones, e.g., dibenzalacetone, etc.; coumarins, e.g., 5,7-dioxycoumarin, etc.; carbostyrils, etc., 1,4-dimethyl-7-oxycarbostyril, etc.; and azoles, e.g., 2-phenylbenzimidazole, 2-(2-hydroxyphenyl)benzotriazole, etc.

In cases where the infrared absorbing composition is filmed by coating, a thin plastic film may be laminated or coated on the coating layer for the purpose of protecting the coating layer or imparting an anti-stick quality to the coating layer. For example, a 0.05 mm thick polyvinyl chloride film can be laminated on the coating under pressure at 120° to 140° C. to obtain a laminated film.

The amount of the compounds represented by formulae (I) to (III) in the infrared absorbing composition of the invention ranges from 0.1 to 50 parts by weight, and preferably from 0.5 to 10 parts by weight, per 100 parts by weight of the binder. The optical filters obtained from the infrared absorbing composition of the invention may have a low transmittance in the wavelength region that should be shielded for a particular use as long as they perform their purpose. It is necessary to control the amount of the compounds of formulae (I) to (III) to be added and the thickness of the filter so that transmittance in the wavelength region of 600 nm or more would be 10% or less, preferably 2.0% or less, and more preferably 0.1% or less. A practical thickness of the filter is usually from 0.002 to 0.5 mm, but a thickness outside of this range may also be used depending on the final use.

The near infrared absorbing compositions according to the present invention have absorption maxima at a wavelength of about 600 nm or more and can be formed into optical filters excellent in resistance to heat and light at low cost. Further, solvent solubility of the metal complexes according to the present invention can be controlled by appropriately selecting a cation species to be combined with the complex ion. Therefore, a wide variety of binders can be used in the preparation of the infrared absorbing composition.

The optical filters obtained from the infrared absorbing composition of the present invention can be applied to the above-described uses, such as safelight filters for infrared-sensitive photographic materials, agricultural films, that radiation shields, infrared light cut filters for human eyes, infrared light cut filters for semi-conductor photoreceptors, infrared light cut filters for optoelectronic integral circuits having an element having electric functions combined with optical functions on the same base, as well as many other uses.

The compositions according to the present invention are also applicable to other uses taking advantage of their infrared absorption characteristics. For example, they can be used in infrared absorbing coatings; inks for ink jet printers as described in Japanese patent application (OPI) No. 135568/81 to improve efficiency of reading with near infrared rays; and laser ray recording and reading media as described in Japanese patent application (OPI) No. 11090/82.

In addition, they can be utilized as infrared ray-heat exchanging media taking advantage of their property to convert near infrared rays to heat. Typical examples of the infrared ray-heat exchanging media include:

(1) laser heat-sensitive recording materials as described in Japanese patent application (OPI) Nos. 14095/82 and 14096/82 in which the composition of the invention enhances a color developing induced by heat generated by infrared laser irradiation, (2) resist materials having solubility variable by the action of heat generated by laser rays as described in Japanese patent application (OPI) No. 40256/82, and (3) thermodrying or thermosetting compositions as described in Japanese patent application (OPI) No. 143342/81 in which the composition of the invention accelerates the thermal reaction.

Furthermore, the compounds according to the present invention can be utilized in electrophotographic light-sensitive films for electrophotographic printers using semi-conductor lasers as a light source as described in Japanese patent application (OPI) No. 214162/83 or films for photo discs for writing and reading with semi-conductor lasers.

The foregoing examples of applications have been given for illustrative purposes only and do not limit the applications of the compounds or compositions according to the present invention.

The present invention will now be illustrated in greater detail by way of examples, but it should be understood that they are not deemed to limit the present invention. In these examples, all the parts are by weight unless otherwise indicated.

EXAMPLE 1

| | |
|---|---|
| Triacetyl cellulose (TAC) | 170 parts |
| Triphenyl phosphite (TPP) | 10 parts |
| Methylene chloride | 800 parts |
| Methanol | 160 parts |
| Compound (2) | 2 parts |

Figure 1:
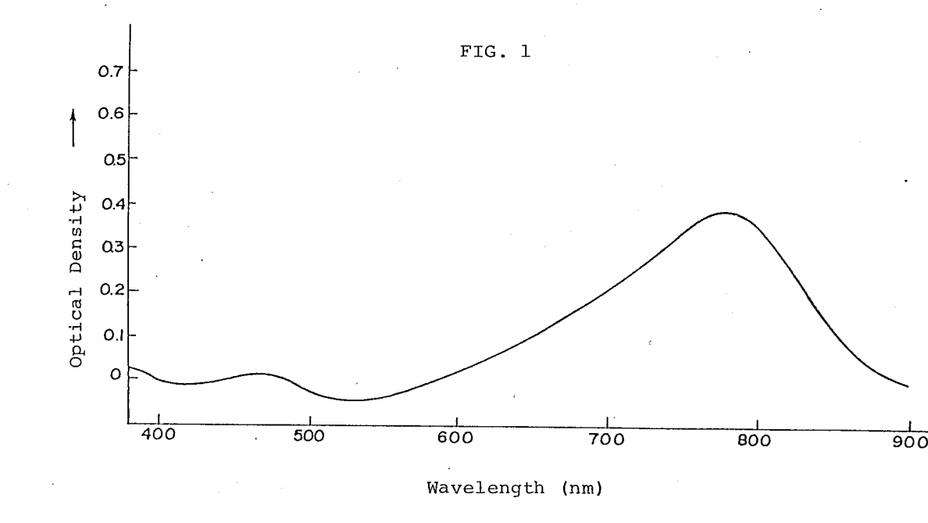
FIGS. 1 to 3 each shows an optical density curve of an optical filter prepared by using the infrared absorbing composition according to the present invention.

The above components were mixed by stirring well and filtered. The resulting composition was cast on a metal substrate to a varying thickness. After hardening, the cast film was stripped off to obtain optical filters having a dry thickness of from 0.02 to 0.3 mm. The optical density of the optical filter having a thickness of 60 μm is shown in Fig. 1.

EXAMPLE 2

Figure 2:
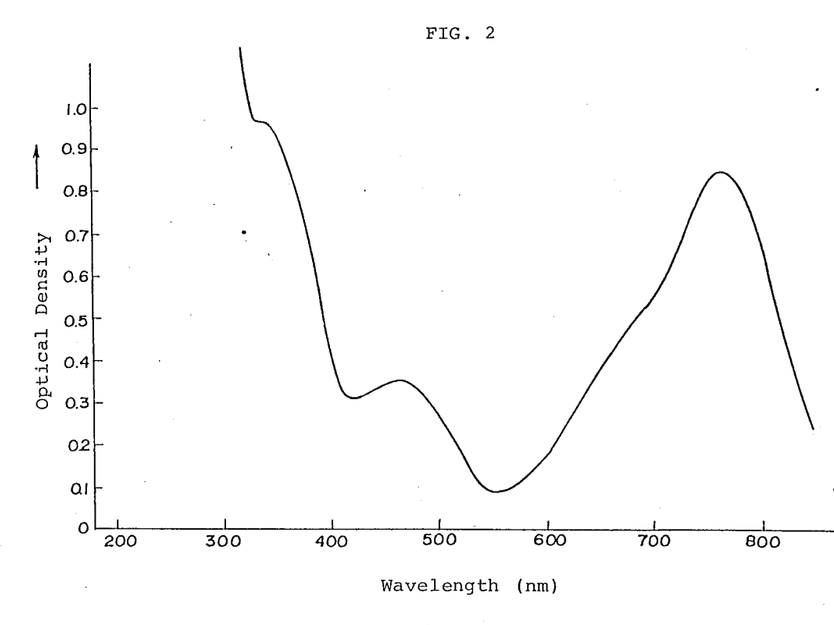

Optical filters having a dry thickness between 0.02 mm and 0.3 mm were prepared in the same manner as in Example 1 except for replacing Compound (2) with Compound (21). The optical density of the film having a thickness of 60 μm is shown in FIG. 2.

EXAMPLE 3

Figure 3:
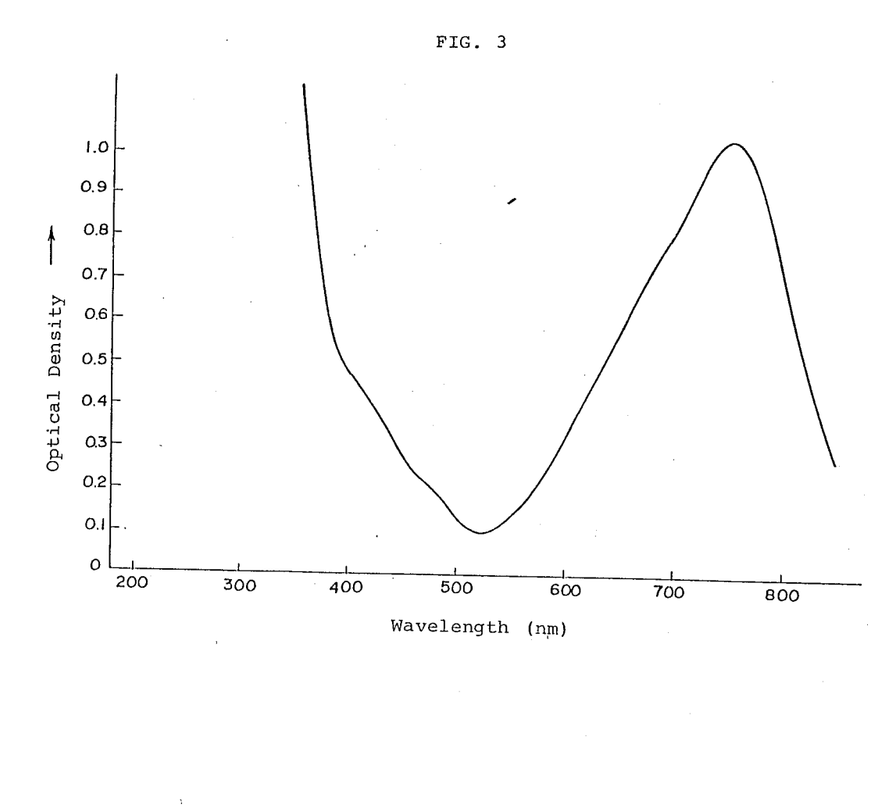

Optical filters having a dry thickness between 0.02 mm and 0.3 mm were prepared in the same manner as in Example 1, except for replacing Compound (2) with Compound (115). The optical density of the film having a thickness of 95 μm is shown in FIG. 3.

EXAMPLE 4

A 0.19 mm thick optical filter was prepared in the same manner as in Example 1, except that the composition to be cast further contained 0.2 part of 2-(5-t-butyl-2-hydroxyphenyl)benzotriazole as an ultraviolet absorbent.

In order to evaluate the effect of the ultraviolet absorbent on light-resistance, each of the optical filters prepared in Examples 1 and 4 was exposed to light of a xenon lamp (120,000 lux) for 24 hours, and the change in optical density at a wavelength of 781 nm was measured. The results obtained are shown in Table 2 below.

TABLE 2

| | Optical Density | |
|---|---|---|
| Example No. | Before Light Exposure | After Light Exposure |
| 1 | 0.93 | 0.64 |
| 2 | 0.93 | 0.83 |

It can be seen from Table 2 that a combination of the compound according to the present invention and an ultraviolet absorbent markedly improves light resistance of the optical filter.

EXAMPLE 5

A composition comprising Compound (2), a thermosetting acrylic resin, and dimethylformamide at a weight ratio of 1:4:6 was coated on a 0.5 mm thick transparent glass substrate to a wet thickness of 2 μm, followed by heating at 150° C. for 20 minutes to form an infrared shielding layer.

The infrared shielding layer was coated with a chromium nitride layer to a thickness of 500 Å by sputtering, and a chromium layer was further deposited thereon by sputtering. A resist ("AZ-1450" produced by Shipley Co., Ltd) was then formed on the chromium layer. The resist was exposed to light through a photomask, developed, and dried. The exposed chromium layer and chromium nitride layer were removed by etching with an etching solution containing ammonium cerium nitrate. Thereafter, the resist layer was stripped off to obtain a photo-shielding layer having a prescribed pattern on the infrared shielding layer. The thus obtained photo-shielding layer was free from the problem of flare because the reflectance of the glass surface was 15% or less.

A water-soluble light-sensitive composition comprising casein and ammonium bichromate was coated on the infrared shielding layer having the photo-shielding layer to a thickness of 0.8 μm and dried. A photomask having a prescribed pattern was intimately contacted with the thus formed light-sensitive layer in an accurate position, exposed to light, and developed with warm water to form a patterned layer. This layer was dyed in red with a red dye bath having the following formulation to form a red-colored layer (hereinafter referred to as the R layer). After treating the R layer to impart resistance to dyeing, a green-colored layer (the G layer) and a blue-colored layer (the B layer) each having a thickness of 0.8 μm were formed on the infrared shielding layer having the photo-shielding layer in the same manner as described above, except for using a green dye bath and a blue dye bath each having the following formulation, respectively, in place of the red dye bath to obtain a color separation filter layer composed of R, G and B layers.

| | |
|---|---|
| Red Dye Bath Formulation: | |
| Kayanol Milling Red RS (produced by Nippon Kayaku Co., Ltd.) | 1 part |
| Acetic acid | 3 parts |
| Water | 100 parts |
| Green Dye Bath Formulation: | |
| Brilliant Indo Blue (produced by Hoechst) | 1 part |
| Suminol Yellow MR (produced by Sumitomo Chemical Co., Ltd.) | 1 part |
| Acetic acid | 3 parts |
| Water | 100 parts |
| Blue Dye Bath Formulation: | |
| Kayanol Cyanine 6B (produced by Nippon Kayaku Co., Ltd.) | 1 part |
| Acetic acid | 3 parts |
| water | 100 parts |

An acrylic resin was coated on the color separation filter layer to a thickness of 1 μm to form a protective layer. The color separation filter chip had the same size as the light-sensitive area of a solid image forming element. The resulting color separation filter showed excellent performance in shielding longer wavelength light of 700 nm or more.

EXAMPLE 6

| | |
|---|---|
| Compound (115) | 1 g |
| Nitrocellulose | 0.2 g |
| Dichloromethane | 7 ml |

A solution comprising the above components was applied on a glass plate by rotational coating and dried at 40° C. to form a recording layer having a thickness of 0.25 μm. The reflectance and the absorptivity of the recording layer at 780 nm were 19% and 63%, respectively.

When signals of 1 MHz were recorded on the resulting recording medium with a semi-conductor laser beam having a wavelength of 780 nm, an energy of 4 mW at the irradiated surface, and a beam diameter of 1.6 μm, a pit of 1.0 μm in diameter was formed by irradiation for 0.2 micro-second (1.6 nJ/pit). When the recording medium was preserved at a temperature of 60° C. and at a humidity of 90% under a room light for 1 month, no change in recording and reading performances was observed.

EXAMPLE 7

| Compound (21) | 1 g |
|---|---|
| Polycarbonate resin | 1.0 g |
| C.I. Acid Blue 83 (C.I. 42630) | 0.8 g |
| 1,2-Dichloroethane | 12 ml |

A solution comprising the above components was coated by rotation on an acrylic resin plate whose surface had been hardened, followed by heating at 60° C. to form a recording layer having a thickness of 0.24 μm. The reflectance and the absorptivity of the recording layer at 780 nm were 12% and 40%, respectively, and those at 630 nm were 20% and 36%, respectively. When signals of 0.4 MHz were recorded on the resulting recording medium with a semiconductor laser beam having an energy of 6 mW at the irradiated surface, a beam diameter of 1.6 μm, and a wavelength of 780 nm, a pit of 1.0 μm in diameter was formed by irradiation for 0.5 micro-second (6.0 nJ/pit). Further, when signals of 4 MHz were recorded on the recording medium with a He-Ne laser beam having a beam diameter of 1.6 μm and an energy of 5 mW at the irradiated surface, a pit of 1.0 μm in diameter was formed by irradiation for 0.4 micro-second (1.6 nJ/pit).

When the recording medium was preserved under the same conditions as in Example 6, no change in performances was observed.

EXAMPLE 8

| Compound (21) | 1 g |
|---|---|
| Dichloromethane | 20 ml |

A coating composition comprising the above components was coated by rotation on a plate of polymethyl methacrylate having a tridimensional polymer structure and dried at 40° C. There was obtained a flat recording layer of 0.24 μm in thickness without using any binder. The reflectance and the absorptivity of the recording layer at 780 nm were 19% and 62%, respectively.

When signals of 4 MHz were recorded on the resulting recording medium with a semiconductor laser beam having a wavelength of 780 nm, an energy of 4 mW on the irradiated surface, and a beam diameter of 1.6 μm, a pit of 1.0 μm in diameter was formed by irradiation for 0.25 micro-second (1.2 nJ/pit). When the recording medium was prepared at a temperature of 60° C. and at a humidity of 90% under a room light for 1 month, no change in recording and reading performances was observed.

EXAMPLE 9

| Compound (38) | 1 g |
|---|---|
| Polycarbonate resin | 0.7 g |
| C.I. Acid Blue 83 (C.I. 42630) | 0.8 g |
| 1,2-Dichloroethane | 12 ml |

A solution comprising the above components was coated by rotation on a polycarbonate plate on which an ultraviolet-curing resin had been coated and cured, followed by drying at 60° C. to form a 0.4 μm thick recording layer. The reflectance and the absorptivity of the recording layer at 780 nm were 16% and 51%, respectively, and those at 630 nm were 14 and 62%, respectively.

When signals of 0.4 MHz were recorded on the resulting recording medium with a semiconductor laser beam having an energy of 6 mW at the irradiated surface, a beam diameter of 1.6 μm, and a wavelength of 1.6 μm, a pit of 1.0 μm in diameter was formed by irradiation for 0.4 micro-second (1.8 nJ/pit). Further, when signals of 4 MHz were recorded with a He-Ne laser beam having a beam diameter of 1.6 μm and an energy of 5 mW on the irradiated surface, a pit of 0.8 μm in diameter was formed by irradiation for 0.4 micro-second (1.6 nJ/pit).

When the recording medium was preserved under the same conditions as in Example 8, no change in performances was observed.

EXAMPLE 10

| Cellulose acetate butyrate | 0.8 g |
|---|---|
| Acetone | 32 ml |

A solution comprising the above components was coated by rotation on a polycarbonate disc to form a subbing layer having a dry thickness of 0.1 μm.

| Compound (21) | 1 g |
|---|---|
| Polyvinyl formal | 0.7 g |
| Dichloromethane | 10 g |

A solution comprising the above components was coated by rotation on the subbing layer to form a recording layer having a dry thickness of 0.4 μm. Silver was vacuum evaporated onto the recording layer to a thickness of 0.1 μm. Two of the resulting coated discs were brought together so that the silvered surfaces faced toward each other with spacers being interposed therebetween at the central and peripheral positions to obtain a sandwich structure recording medium.

A semiconductor laser beam having a wavelength of 780 nm and a beam diameter of 1.6 μm was irradiated on the resulting recording medium from the polycarbonate side at an energy of 6 mW on the irradiated surface. There was formed a pit of 0.9 μm in diameter by irradiation for 0.5 microsecond (4.2 nJ/sec.).

When the recording medium was preserved at a temperature of 80° C. and a humidity of 90% under a room light for 2 months, no change in recording and reading performances was observed.

EXAMPLE 11

| Compound (115) | 1.0 g |
|---|---|
| Polyvinyl formal | 0.7 g |
| Dichloromethane | 12 ml |

A solution comprising the above components was coated by rotation on a polycarbonate resin plate on which aluminum had been vacuum evaporated to a thickness of 0.04 μm, followed by drying to obtain a light-absorbing layer having a thickness of 0.4 μm. The reflectance and the absorptivity of the resulting recording medium at a wavelength of 780 nm were 16% and 64%, respectively. When signals of 2 MHz were recorded on the recording medium with a semiconductor laser beam having a wavelength of 780 nm, an energy of 6 mW at the irradiated surface, and a beam diameter of 1.6 μm from the base side, a pit having a diameter of 0.8 μm was formed by irradiation for 0.5 micro-second (3.0 nJ/pit). When the recording medium was preserved at a temperature of 60° C. and a humidity of 90% for 1 month, the recording and reading performances underwent no deterioration.

EXAMPLE 12

| Nitrocellulose | 0.4 g |
|---|---|
| Dichloromethane | 10 ml |

A solution comprising the above components was coated by rotation on a cell-cast acrylic resin plate to form a subbing layer. Onto the subbing layer, Compound (2) was vacuum evaporated to a thickness of 0.24 μm. A solution of 0.5 of gelatin in 10 ml of water was then coated thereon by rotational coating to form a protective layer of 0.5 μm in thickness. When a laser beam having a wavelength of 780 nm was irradiated on the resulting recording medium from the base side in the same manner as in Example 10, a pit of 0.9 μm in diameter was formed by irradiation for 0.5 microsecond (2.0 nJ/pit). When the recording medium was preserved at a temperature of 60° C. and a humidity of 90% under a room light for 1 month, no change in performances was observed.

EXAMPLE 13

Compound (2) was vacuum evaporated onto a cell-cast acrylic resin card through a mask having a stripe-shaped opening at a rate of 300 Å/min to form a deposit layer having a thickness of 0.1 μm. A 5 wt% gelatin aqueous solution was then coated on the entire surface of the card to prepare a laser card.

The thickness of the deposit layer was measured by utilizing changes in frequency of a quartz oscillator with the specific gravity of Compound (2) being set at 1.3. The deposit layer had very good film properties and did not easily fall off from the acrylic resin plate. The reflectance from the base at 780 nm was 22%. When signals of 4 MHz were recorded on the laser card with a laser beam having a wavelength of 780 nm, an energy of 5 mW on the irradiated surface, and a beam diameter of 1.6 μm, a pit having a diameter of 0.8 μm was formed. When the laser card was preserved at a temperature of 70° C. and a humidity of 80% under a fluorescent light for 1 month, no change in recording and reading performances was observed.

When the same procedures were repeated, except for changing the rate of vacuum evaporation to 1000 Å, the deposit layer contained slightly larger particles (particle size: about 0.4 μm), but recording could be carried out with a laser beam having a wavelength of 780 nm, an energy of 5 mW on the irradiated surface, and a beam diameter of 1.6 μm.

While the invention has been described in detail and with reference to specific embodiments thereof, it will be apparent to one skilled in the art that various changes and modifications can be made therein without departing from the spirit and scope thereof.

What is claimed is:

1. An infrared absorbing composition containing a binder and at least one compound selected from compounds represented by formula (I)

wherein $R^1$, $R^2$, $R^3$, $R^4$ and $R^5$, which may be the same or different, each represents a halogen atom, a hydrogen atom, or a substituted or unsubstituted alkyl, aryl, cycloalkyl or heterocyclic group, L is a divalent linking group and n is 0 or 1, or any pair of $R^1$, $R^2$, $R^3$, $R^4$ and $R^5$ adjacent to one another on the same ring combine to form a ring; $R^6$ and $R^7$, which may be the same or different, each represents an alkyl group or a substituted or unsubstituted aryl group; and $R^8$ and $R^9$, which may be the same or different, each represents a hydrogen atom, a substituted or unsubstituted alkyl group, a substituted or unsubstituted aryl group; or $R^8$ and $R^9$ combine for form a substituted or unsubstituted ring, which may be condensed with one or more additional rings or ring systems which may be substituted with substituents;

compounds represented by the formula (II)

(II)

wherein $R^{10}$, $R^{11}$, $R^{12}$, $R^{13}$ and $R^{14}$, which may be the same or different, each represents a halogen atom, a hydrogen atom, or a substituted or unsubstituted alkyl, aryl, cycloalkyl or heterocyclic group, L' is a divalent linking group and m is 0 or 1, or any pair of $R^{10}$, $R^{11}$, $R^{12}$ and $R^{14}$ having adjacent positions on the same ring combine to form a ring; and $R^{15}$ and $R^{16}$, which may be the same or different, each represents a hydrogen atom, a substituted or unsubstituted alkyl group, a substituted or unsubstituted aryl group or a cyano group; or $R^{15}$ and $R^{16}$ combine for form a substituted or unsubstituted ring, which may be condensed with one or more additional rings or ring systems which may be substituted with substituents:

and compounds represented by the formula (III)

(III)

wherein $R^{17}$, $R^{18}$, $R^{19}$, $R^{20}$ and $R^{21}$, which may be the same or different, each represents a halogen atom, a hydrogen atom, or a substituted or unsubstituted alkyl, aryl, cycloalkyl or heterocyclic group, L" is a divalent linking group and p is 0 or 1, or any pair of $R^{17}$, $R^{18}$, $R^{19}$, $R^{20}$, and $R^{21}$ having adjacent positions on the same ring combine to form a ring; and $R^{22}$ and $R^{23}$, which may be the same or different, each represents a hydrogen atom, a substituted or unsubstituted alkyl group, a substituted or unsubstituted aryl group or a cyano group; or $R^{22}$ and $R^{23}$ combine to form a substituted or unsubstituted ring, which may be condensed with one or more additional rings or ring systems which may be substituted with substituents.

2. An infrared absorbing composition as in claim 1, wherein said compound or compounds is or are present in a total amount of from 0.1 to 50 parts by weight per 100 parts by weight of a binder.

3. An infrared absorbing composition as in claim 2, wherein said compound or compounds is or are present in a total amount of from 0.5 to 10 parts by weight per 100 parts by weight of a binder.

4. An infrared absorbing composition as in claim 1, wherein said composition has a transmittance of 10% or less at a wavelength of 600 nm or more.

5. An infrared absorbing composition as in claim 4, wherein said composition has a transmittance of 2.0% or less at a wavelength of 600 nm or more.

6. An infrared absorbing composition as in claim 5, wherein said composition has a transmittance of 0.1% or less at a wavelength of 600 nm or more.

7. An infrared absorbing composition as in claim 1, wherein at least one of $R^1$, $R^2$, $R^3$, $R^4$, $R^5$, $R^{10}$, $R^{11}$, $R^{12}$, $R^{13}$, $R^{14}$, $R^{17}$, $R^{18}$, $R^{19}$, $R^{20}$ and $R^{21}$ is an alkyl group which contains from 1 to 20 carbon atoms.

8. An infrared absorbing composition as in claim 1, wherein at least one of $R^1$, $R^2$, $R^3$, $R^4$, $R^5$, $R^{10}$, $R^{11}$, $R^{12}$, $R^{13}$, $R^{14}$, $R^{17}$, $R^{18}$, $R^{19}$, $R^{20}$ and $R^{21}$ is an aryl group which contains from 6 to 14 carbon atoms.

9. An infrared absorbing composition as in claim 1, wherein at least one of $R^1$, $R^2$, $R^3$, $R^4$, $R^5$, $R^{10}$, $R^{11}$, $R^{12}$, $R^{13}$, $R^{14}$, $R^{17}$, $R^{18}$, $R^{19}$, $R^{20}$ and $R^{21}$ is a 5- or 6-membered heterocyclic ring.

10. An infrared absorbing composition as in claim 1, wherein at least one of $R^1$, $R^2$, $R^3$, $R^4$, $R^5$, $R^{10}$, $R^{11}$, $R^{12}$, $R^{13}$, $R^{14}$, $R^{17}$, $R^{18}$, $R^{19}$, $R^{20}$ and $R^{21}$ is a 5- or 6-membered cycloalkyl group.

11. An infrared absorbing composition as in claim 1, wherein at least two adjacent groups of $R^1$, $R^2$, $R^3$, $R^4$, $R^5$, $R^{10}$, $R^{11}$, $R^{12}$, $R^{13}$, $R^{14}$, $R^{17}$, $R^{18}$, $R^{19}$, $R^{20}$ and $R^{21}$ form a 6-membered ring.

12. An infrared absorbing composition as in claim 11, wherein said 6-membered ring is a benzene ring or a benzene ring condensed with one or more additional substituted or unsubstituted rings or ring systems.

13. An infrared absorbing composition as in claim 1, wherein at least one of $R^1$, $R^2$, $R^3$, $R^4$, $R^5$, $R^{10}$, $R^{11}$, $R^{12}$, $R^{13}$, $R^{14}$, $R^{17}$, $R^{18}$, $R^{19}$, $R^{20}$ and $R^{21}$ is bonded to said carbon atom of said benzene ring via a divalent linking group selected from the group consisting of an oxy group, a thio group, an amino group, an oxycarbonyl group, a carbonyl group, a carbamoyl group, a sulfamoyl group, a carbonylamino group, a sulfonyl group, and a carbonyloxy group.

* * * * *